US009410890B2

(12) United States Patent
Sappey

(10) Patent No.: US 9,410,890 B2
(45) Date of Patent: Aug. 9, 2016

(54) METHODS AND APPARATUS FOR SPECTRAL LUMINESCENCE MEASUREMENT

(71) Applicant: KLA-Tencor Corporation, Milpitas, CA (US)

(72) Inventor: Romain Sappey, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 93 days.

(21) Appl. No.: 13/796,948

(22) Filed: Mar. 12, 2013

(65) Prior Publication Data

US 2013/0242300 A1 Sep. 19, 2013

Related U.S. Application Data

(60) Provisional application No. 61/612,669, filed on Mar. 19, 2012.

(51) Int. Cl.
*G01N 21/00* (2006.01)
*G01N 21/64* (2006.01)
(Continued)

(52) U.S. Cl.
CPC ............ *G01N 21/6489* (2013.01); *G01B 11/06* (2013.01); *G01N 21/66* (2013.01)

(58) Field of Classification Search
CPC ... H01J 37/32935; G01N 21/64; G01N 21/65; G01N 21/68; G01N 2105/1037; G01J 3/02
USPC ....................................................... 356/72–73
See application file for complete search history.

(56) References Cited

U.S. PATENT DOCUMENTS 6,429,968 B1 8/2002 Carver
7,362,426 B1 4/2008 Yoo
(Continued)

FOREIGN PATENT DOCUMENTS

EP    1 619 640 A1   1/2006
RU    2412452 C2     2/2011

OTHER PUBLICATIONS

Hums et al. "Fabry-Perot effects in INGaN/GaN heterostructures on Si-substrate", Feb. 2007, Journal of Applied Physics, vol. 101, pp. 33113-033113.*

(Continued)

*Primary Examiner* — Abdullahi Nur
(74) *Attorney, Agent, or Firm* — Okamoto & Benedicto LLP

(57) ABSTRACT

One embodiment relates to a computer-implemented method of processing spectral luminescence mapping data obtained from a substrate, the substrate having an epitaxial layer stack that includes a multiple quantum well. A spectral luminescence and an epi thickness at a location on the substrate are obtained. A spectral modulation for the location may be computed given the epi thickness and material indices of refraction. The underlying luminescence spectrum may then be generated by dividing the measured spectral luminescence by the spectral modulation. Subsequently, a peak wavelength and other parameters may be obtained from the underlying luminescence spectrum. In another embodiment, the underlying luminescence spectrum may be determined, without the epi thickness measurement, using a self-consistent technique. Another embodiment relates to an apparatus for spectral luminescence mapping and epitaxial thickness measurement. Other embodiments, aspects and features are also disclosed.

14 Claims, 7 Drawing Sheets

(51) Int. Cl.
*G01B 11/06* (2006.01)
*G01N 21/66* (2006.01)

(56) References Cited

U.S. PATENT DOCUMENTS

| | | | |
|---|---|---|---|
| 2002/0093648 A1* | 7/2002 | Nikoonahad et al. | 356/237.1 |
| 2010/0221025 A1 | 9/2010 | Takahashi | |
| 2012/0025097 A1* | 2/2012 | Meloni | G01N 21/6489 250/458.1 |
| 2012/0049085 A1 | 3/2012 | Sappey et al. | |

OTHER PUBLICATIONS

Costantino S. Martinez, et al "Wide band interferometry for thickness measurement", Apr. 2013, 2 sheets, Optics Express, vol. 11, No. 8.

G. Khitrova, et al "Nonlinear optics of normal-mode-coupling semiconductor microcavities", Oct. 1999, 2 sheets, Reviews of Modern Physics, vol. 71, No. 5.

Robert Herrick, et al "Using broadband reflectometry for fast trench-depth measurement", Feb. 2013, 7 sheets, Solid State Technology insights for electronics manufacturing.

Steven E.J. Bell, et al "Analysis of luminescent samples using subtracted shifted Raman spectroscopy", Aug. 1998, Analyst (RSC Publishing).

Hosea, et al. "Analysis of reflectance and modulation spectroscopic lineshapes in optoelectronic device structures", 2006, 4 sheets, Applied Surface Science.

PCT International Search Report and Written Opinion of the International Searching Authority for Application No. PCT/US2013/032985, Jul. 18, 2013, 10 sheets.

C. Hums, et al "Fabry-Perot effects in InGaN/GaN heterostructures on Si-substrate", 2007, 4 pages, Journal of Applied Physics 101, American Institute of Physics.

extended European search report for Application No. EP 13 765 167.5, Sep. 25, 2015, 8 sheets.

* cited by examiner

FIG. 2    200

METHODS AND APPARATUS FOR SPECTRAL LUMINESCENCE MEASUREMENT

CROSS-REFERENCE TO RELATED APPLICATION(S)

The present application claims the benefit of U.S. Provisional Patent Application No. 61/612,669, filed Mar. 19, 2012, entitled "Methods and Apparatus for Simultaneous Thickness and Spectral PL Mapping," the disclosure of which is hereby incorporated by reference.

BACKGROUND

1. Technical Field

The present invention relates generally to the field of spectral photoluminescence mapping on transparent films, such as these found in Light Emitting Diodes (LED). The present invention may also be applicable to spectral electroluminescence mapping on transparent films. The substrate the films are deposited on may be transparent or opaque.

2. Description of the Background Art

Photoluminescence (PL) and electroluminescence (EL) are spectroscopy techniques providing information on electrical and optical properties of semiconductor materials, such as bandgap, emission wavelength, composition, defects, and so on. A PL mapper is a laser-based instrument used to generate parameter maps over a wafer by measuring optical luminescence emission from materials excited with energy above their bandgap. An EL mapper excites excess carriers using direct current injection, rather than a laser source. An EL mapper is typically used on final devices where electrical contact pads already exist, but may also be used on an epi layer after the MOCVD deposition step. The value of the EL measurement is that it adds electrical properties to the luminescence measurement, such as the forward voltage, the reverse current, or the I(V) curve of the junction that will constitute the heart of the finished LED.

A typical light emitting diode (LED) wafer after metal organic chemical vapor deposition (MOCVD) of the active layers includes the substrate (typically a sapphire wafer from two to six inches in diameter), GaN buffer layers (to help accommodate the lattice mismatch between the sapphire and the critical layers), a negatively doped (n-GaN) contact layer, a multi-quantum well (MQW) multilayer hetero-structure, an optional electron blocking layer and a positively doped (p-GaN) contact layer.

Metrology tools that sample an entire area of the LED epitaxial (epi) layer post-MOCVD may be referred to as a photoluminescence (PL) mapper. The operating principle of these tools involves exciting the MQW at shorter wavelength than the emission wavelength hereby generating electron-hole pairs in the active region and detecting the spectral emission line from the radiative recombination of electrons and holes as a function of the location on the wafer. PL mappers may report important statistics describing the local luminescence spectra, such as: peak wavelength, peak intensity and full-width at half-maximum (FWHM) of the local emission spectrum observed. The typical spatial resolution for such mapping is on the order of one millimeter, which is generally sufficient for the typical spatial variations of the emission wavelength, as these variations are mainly coming from MOCVD temperature gradients which occur at millimeter and longer length scales. The "peak wavelength" is typically measured over the whole area of all the epi wafers from an MOCVD deposition run, and used by process control engineers to directly flag the temperature gradients that existed in the MOCVD process for that wafer: The typical wavelength shift expected is on the order of approximately 2 nanometers per degree Kelvin (nm/K), and it thus only takes a deposition temperature gradient on the order of one degree to affect the bin yield for the final devices. Accordingly, very tight temperature drift and gradient control are mandated at the elevated growth temperature found in the reactor, and a systematic control for each outgoing wafer is needed as its individual temperature uniformity is also a function of how well that wafer sat in the MOCVD carrier pocket. A large range of peak wavelength variations within a given wafer may be indicative that the MOCVD reactor's wafer carrier needs to be cleaned or replaced. The FWHM and peak intensity (brightness) are also important and may be related to the quality and uniformity of the epi layer and MQW composition and structure.

SUMMARY

Figure 1:
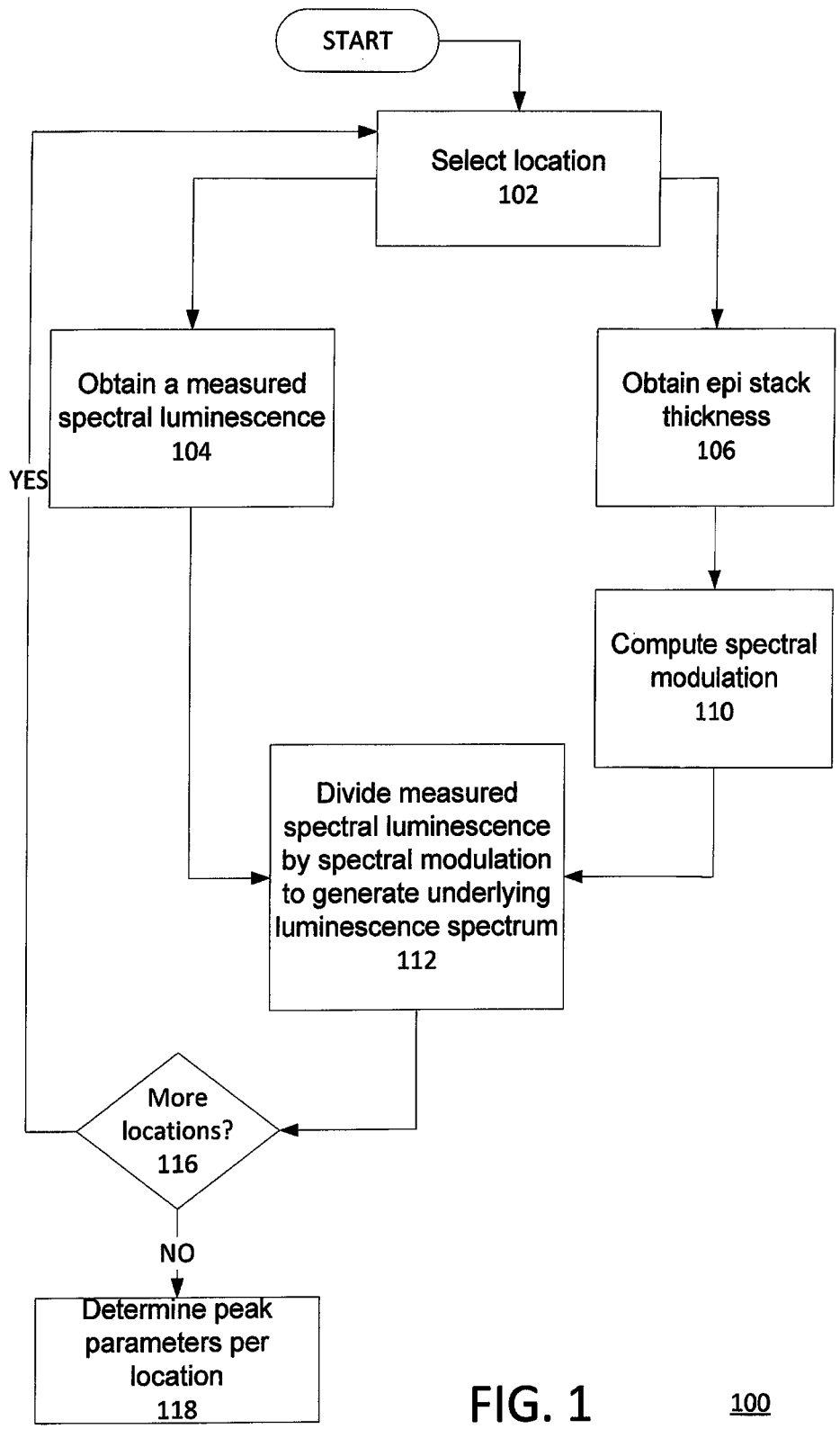
FIG. 1 is a flow chart of a first method of underlying peak extraction for spectral luminescence mapping in accordance with an embodiment of the invention.

One embodiment relates to a computer-implemented method of processing spectral luminescence mapping data obtained from a substrate, the substrate having an epitaxial layer stack that includes a multiple quantum well. The proposed processing aims at removing the spectral modulations due to thickness effects (optical cavity) that adversely affect the measured luminescence spectrum. A luminescence spectrum and an epi thickness at a location on the substrate are obtained. An initial underlying luminescence spectrum may be set, and a spectral modulation for the location may be computed given the epi thickness and the material indices of refraction. The underlying luminescence spectrum may then be generated by dividing the measured spectral luminescence by the spectral modulation. Subsequently, an accurate peak wavelength and other parameters may be obtained from the underlying luminescence spectrum.

In another embodiment, the underlying luminescence spectrum may be determined, without the epi thickness measurement, using a self-consistent technique. In this technique, a line shape for an underlying local luminescence spectrum may be constrained (e.g. to a Gaussian profile), and the position, FWHM, and peak intensity of the underlying local luminescence spectrum may be determined by minimizing the difference between a computed spectral luminescence and the measured spectral luminescence for each location, using the epi layer thickness as an optimization parameter. The local epi thickness value obtained after convergence of the method can then also be provided, which constitutes an epi thickness measurement that may be of additional value.

Another embodiment relates to an apparatus for spectral luminescence mapping and epitaxial thickness measurement. The apparatus may include a stage for holding a target substrate, a laser source outputting a laser beam, a broad-band light source, a photoluminescence detector, an epitaxial thickness detector, and an arrangement of optical elements. The arrangement of optical elements is configured to direct the laser beam from the laser source and the light from the broad-band source onto a surface of the target substrate and to direct scattered laser light to the photoluminescence detector and scattered broad-band light to the epitaxial thickness detector.

Other embodiments, aspects and features are also disclosed.

DETAILED DESCRIPTION

Applicant believes that current PL mapping solutions have disadvantages and limitations in their measurement of peak wavelength, FWHM and peak intensity. Limitations to current PL mappers include the following:

1) The accuracy of current PL mappers is typically insufficient for feed forward use at the die level. Feed-forward is important as it may allow prediction of the luminescence properties of the final LED dies once singulated and contacted, which may be several weeks later than the MOCVD process step. For PL feed-forward use at the die level, the local peak wavelength accuracy needs to be typically a fraction of the targeted color bins for the final device (LED). That means approximately 0.5 nm PL wavelength accuracy is required for 4 nm bins and less for future 2 nm bins for solid state lighting (SSL);

2) Current PL mappers generate PL spectra that have undesirable modulation (fringes). These undesirable fringes are thickness-related fringes. Because of the index mismatch between the substrate (typically, sapphire, n~1.78 in the blue region) and the epi layer (effective structure approximated to just GaN, n approximately 2.5 in the blue region), the MQW structure is within what is optically equivalent to a Fabry-Perot cavity. Applicant has determined that that the Fabry-Perot cavity causes the thickness-related fringes in a typical wavelength band that is about 20 nm at FWHM, corresponding to the PL emission from the MQW structure; and 3) Fourier filtering and other types of signal processing and filtering techniques that may be used by current PL mappers are unsatisfactory in removing the thickness-related fringes. Furthermore, these conventional filtering techniques typically have the undesirable effect of shifting the peak wavelength parameter obtained after the filtering step. A typical shift may be in the range from 0.5 nm to 2 nm. Such a shift of the peak wavelength prevents accurate prediction of the wavelength bins of the light emitted after full fabrication of the device given the need for 0.5 nm or better PL accuracy highlighted above. The inaccuracy also extends to the FWHM and the peak intensity that are extracted from the measured luminescence spectrum.

While the above-discussed limitations exist with the all the main material systems used in the industry (flat sapphire, SiC, Si), the degree of severity varies. The limitations are less problematic for patterned sapphire substrates for which the substrate-epi interface reflectivity is reduced. The limitations are most severe in the case of GaN-on-Si because of the high interfacial reflectivity of the GaN/Si interface, resulting in a very pronounced and problematic modulation of the measured luminescence spectrum.

The method proposed here can accurately reduce or eliminate more accurately the undesirable fringes without causing an unwanted shift in the peak wavelength and other parameters obtained by a PL mapper. Applicant believes that the technique disclosed herein may also be applied to similarly improve electroluminescence (EL) mapping. Such electroluminescence probing may be performed on the final LED die which is typical, but is also sometimes performed right after MOCVD. While the method may yield its best if used in an iterative mode as described in one embodiment, a very fast convergence is expected and very good results may be obtained after the first iteration. The reason the proposed method is preferred over Fourier or other type of filters one may apply, is that the proposed approach is based on actual optical effects, which are physical and can be well calculated. In contrast Fourier or low pass filtering are mathematical operations that ignore the physical origin of the modulation fringes and thus will most likely skew the estimation of the true underlying luminescence spectrum. A reason the skew can be particularly bad is that the fringe spacing as a function of the wavelength is not much smaller than the spectral luminescence feature of interest (luminescence spectrum). The period of the spectral modulation fringes can be of the same order than the FWHM of the underlying spectrum, because of the reduced thickness of the epi layer. It is therefore difficult and not legitimate to just apply a low pass filtering technique, as it will affect the extracted luminescence spectrum. The proposed method is a fully physical approach that allows to legitimately remove large spectral modulations without affecting the underlying signal. In addition, an exemplary embodiment of the technique disclosed herein enables for the efficient measurement of both photoluminescence and thickness simultaneously, as well as detect defects on the surface and measure its topography and reflectivity.

FIG. 1 is a flow chart of a first method 100 of underlying spectrum extraction for spectral luminescence mapping in accordance with an embodiment of the invention. The spectral luminescence mapping data being processed may be obtained from a substrate having an epitaxial layer stack that includes a multiple quantum well. In one embodiment, the spectral luminescence data may be spectral photoluminescence data. In another embodiment, the spectral luminescence data may be electroluminescence data.

The method 100 of FIG. 1 requires measurements of both spectral luminescence data and epi thickness data, where the epi thickness refers to the total thickness of the stack of epitaxial layers and is described further below in relation to FIG. 3. In one embodiment, the spectral luminescence and the epi thickness at each location may be measured simultaneously. In one implementation, the simultaneous measurement may be accomplished using apparatus 600 described below in relation to FIG. 6. In another embodiment, the spectral luminescence and the thickness may be measured separately.

Per block 102, a location on the surface of the substrate may be selected from the spectral luminescence and epi thickness data. In one implementation, the spectral luminescence and epi thickness data includes locations along a spiral scan pattern on the surface of the substrate, and one of these locations may be selected in this step.

Per block 104, a spectral luminescence at the location is obtained. The spectral luminescence may be obtained either by a measurement instrument or from measurement data stored after a previous measurement.

Per block 106, the epi thickness at the location is obtained. The epi thickness may be obtained either by a measurement instrument or from measurement data stored after a previous measurement. In another embodiment, the index of refraction can also be obtained in that step, by using for example an ellipsometric detector.

Per block 110, the spectral modulation may be computed. The spectral modulation for the location may be computed from the epi thickness for the location and the material indices of refraction. The computation of the spectral modulation may be a Fabry-Perot cavity type computation. In some simple cases (Appendix A) it could be analytical and just obtained by a formula. In other cases it may need to be computed numerically, for example by integration over a range of incident ray angles which may better represent the actual optical setup use to perform the measurement.

Per block 112, the underlying luminescence spectrum may be generated. The generation of the underlying luminescence spectrum may be performed, for example, by dividing the measured spectral luminescence for the location by the spectral modulation for the location.

Per block 116, a determination may be made as to whether more locations are to be processed. If there are more locations to be processed, then the method 100 may loop back to select a next location per block 102. If not, then the underlying spectrum extraction for the desired locations on the substrate may be deemed to be complete, and the method 100 may move forward to block 118.

Per block 118, various spectrum parameters may be determined from the underlying luminescence spectra determined for the desired locations. For example, the peak wavelength per location may be determined based on a position of the underlying luminescence spectrum for each location. In addition, a peak intensity, a full-width at half-maximum (FWHM). And any other relevant parameter may be determined based on the obtained underlying luminescence spectrum for each location.

In an alternate embodiment, the measured thickness from block 106 may be used to seed an iterative regression method such as the one described below in relation to block 208 of FIG. 2.

Figure 2:
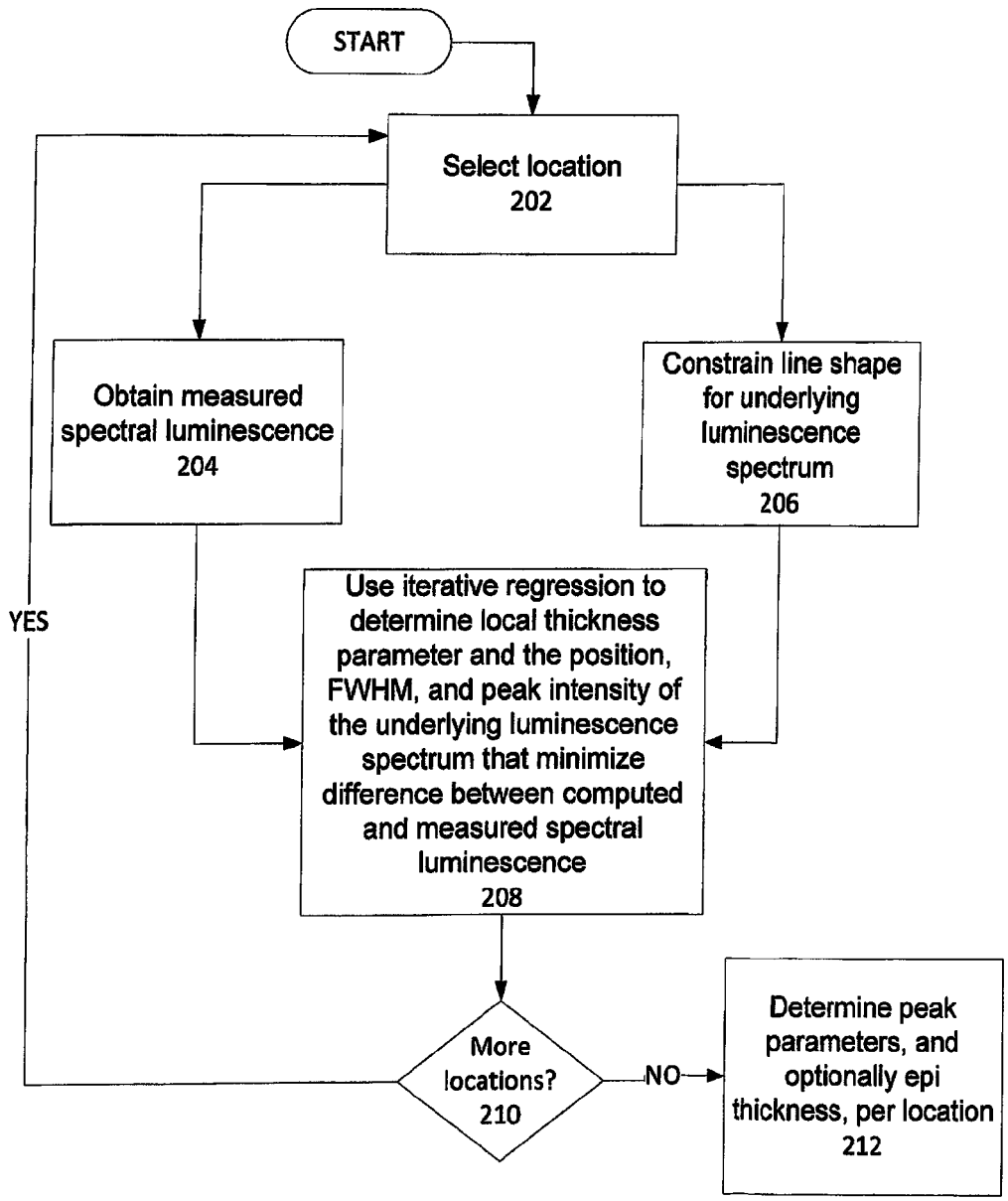
FIG. 2 is a flow chart of a second method of underlying peak extraction for spectral luminescence mapping in accordance with an embodiment of the invention.

FIG. 2 is a flow chart of a second method 200 of underlying peak extraction for spectral luminescence mapping in accordance with an embodiment of the invention. In contrast to the method 100 of FIG. 1, the method 200 of FIG. 2 requires the measured spectral luminescence data, but it does not require the measured epi thickness data.

Per block 202, a location on the surface of the substrate may be selected from the spectral luminescence data. In one implementation, the spectral luminescence data includes locations along a spiral scan pattern on the surface of the substrate, and one of these locations may be selected in this step.

Per block 204, a spectral luminescence at the location is obtained. The spectral luminescence may be obtained either by a measurement instrument or from measurement data stored after a previous measurement.

Per block 206, a functional line shape (but not peak position) for the underlying luminescence peak may be constrained. The line shape may be constrained to a Gaussian shape, for example. Line shapes other than Gaussian may also be used. For example, the line shape used may be obtained from experimental data of similar epi layers on the same type of substrate. A line shape may be any function that can be parametrized and represent the underlying physical luminescence spectrum of the MQW.

Per block 208, using iterative regression, a determination may be made of the local thickness parameter as well as the position, FWHM, and peak intensity of the parametrized line shape that minimize a difference between a computed spectral luminescence and a measured spectral luminescence. In one implementation, a regression procedure may be applied to make this determination. The epi thickness may be used as a free parameter with an initial guess, or be seeded by a priori knowledge (e.g. nominal epi thickness) or a thickness measurement.

Per block 210, a determination may be made as to whether more locations are to be processed. If there are more locations to be processed, then the method 200 may loop back to select a next location per block 202. If not, then the processing to find the underlying luminescence spectrum and epi thickness for the desired locations on the substrate may be deemed to be complete, and the method 200 may move forward to block 212.

Per block 212, various spectrum parameters may be determined from the underlying luminescence spectrums determined for the desired locations. For example, the peak wavelength per location may be determined based on a position of the underlying luminescence spectrum for each location. In addition, a peak intensity and a full-width at half-maximum (FWHM) may be also determined from the underlying luminescence spectrum for each location. Furthermore, the epi thickness may also be (optionally) determined.

Figure 3:
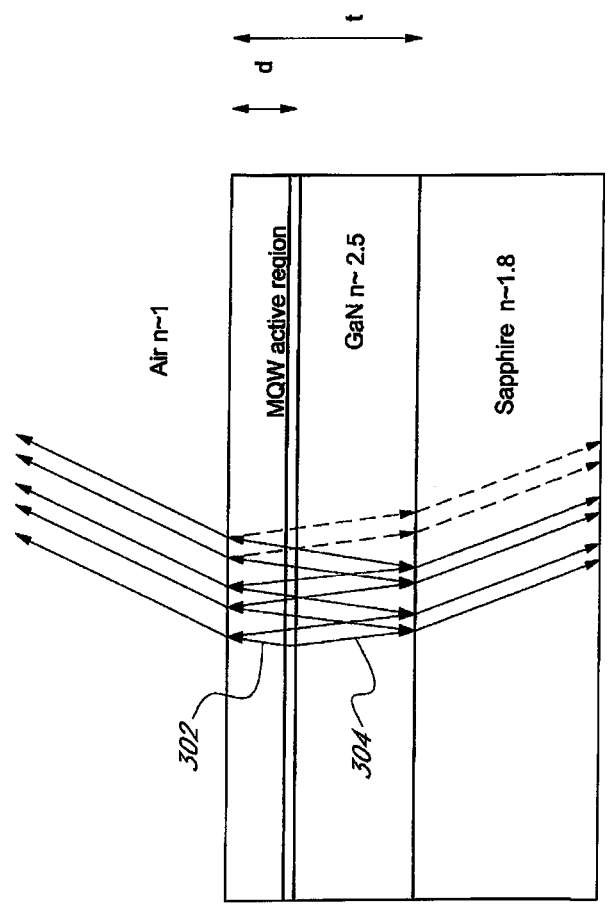
FIG. 3 illustrates a simplified version of an LED epitaxial layer, including a quantum well active region.

FIG. 3 illustrates an LED epitaxial layer including a multiple quantum well (MQW) active region. In this example, the substrate is a sapphire substrate (having an index of refraction, n, of about 1.8), and the epitaxial layer structure of overall thickness t is formed using gallium nitride (GaN) layers (having an index of refraction, n, of about 2.5). The epi thickness t may typically range from about 4 microns to about 9 microns, and the substrate thickness may typically range from 0.4 mm to 1.5 mm.

Within the epitaxial layer structure is the MQW active region which may be an MQW hetero-structure. The epitaxial layers above the MQW active region may have a thickness or depth of d. Above the epitaxial layer structure may be air (having an index of refraction, n, of about 1). Ray paths starting from an upward PL ray 302 and from a downward PL ray 304 are depicted. Just a few rays are shown in this sketch. These rays illustrate the Fabry-Perot cavity optical behavior, with multiple reflections at the interfaces of the cavity, which the light rays emitted by the MQW undergo. A notable difference between the geometry modeled here and a traditional Fabry-Perot cavity is that the luminescence light source is inside the Fabry-Perot cavity, whereas the usual cases are modeling a light source outside the cavity and computing the transmission or reflection coefficient of said cavity.

In accordance with an embodiment of the invention, based on the structure depicted in FIG. 3, a Fabry-Perot cavity type computation may be performed to generate the luminescence fringes or modulation. In one implementation, for the purpose of the Fabry-Perot cavity type computation, the epi stack may be described optically as follows.

First, all layers of the epi stack, except for the MQW structure may be considered to be transparent to radiation in the visible wavelengths, while the MQW structure may absorb and emit light at and below a specified range of wavelengths. For example, the specified range of wavelengths may encompass blue light (i.e. the wavelength range 420 to 480 nm).

Second, all layers within the epi stack may be considered to have a similar or same index of refraction for purpose of simplification. For example, $In_xGa_{1-x}N$ layers in the MQW may be considered to have a same real index of refraction as GaN. The result of this simplification is that the epi stack may behave mainly as one layer of "effective GaN" material and the details of the structure may be ignored in a first (and likely sufficient) approximation. In one implementation, the dispersion of this effective single layer of epi material may be taken, as a first approximation, to be a specific dispersion the dispersion of the primary material for the epi stack (GaN in the above example) with an adjustment factor, where the adjustment factor may be measured using a broadband spectroscopic ellipsometer, for example.

The equations shown in Appendix A relate to a simplified computation of photoluminescence fringes in accordance with an embodiment of the invention. In this simplified computation per Appendix A, the spectral modulation or spectral fringes may be represented by the prefactor derived in front of $I_{PL}$ in the expression we derive in a simple example for the total PL light emitted $I_{total}(\lambda,t)$. As disclosed herein, the expression of this type of physical prefactor may be used to remove the wavelength-dependent thickness effects and more accurately extract the underlying PL emission. In its most complete implementation, the effect may need to be computed numerically, for example, by integration over a range of incident ray angles on the samples, to properly account for the real optical system in which it is being used. It is also possible that the MQW itself reabsorbs a bit of the luminescence light, which could be modeled, in one embodiment of the proposed method, by adding a small imaginary part to the effective index of refraction of GaN.

Figure 4:
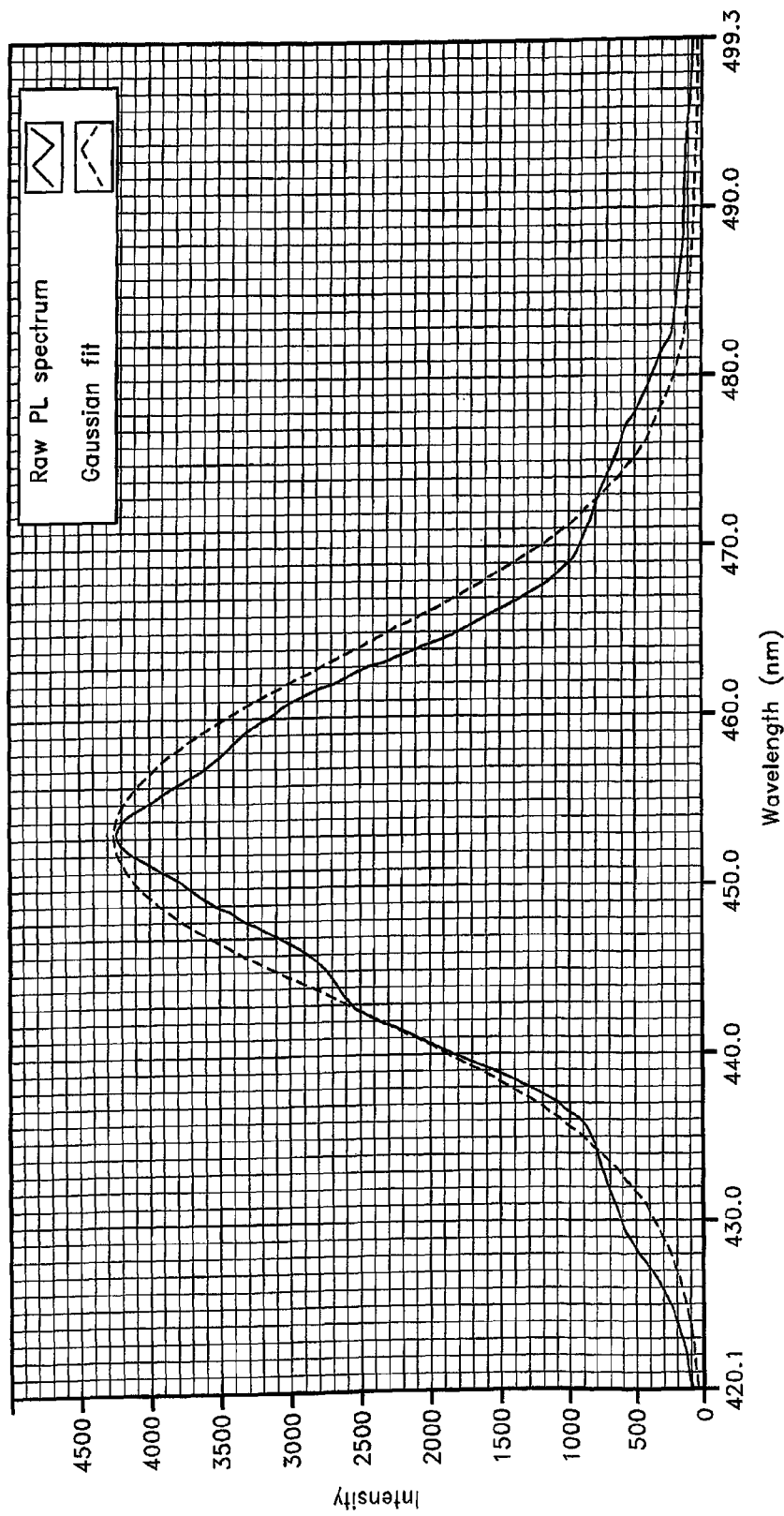
FIG. 4 shows a Gaussian fit to a measured photoluminescence spectrum.

FIG. 4 shows a Gaussian fit to a measured photoluminescence spectrum. In this example, the measured ("raw") PL spectrum is obtained from GaN epi on sapphire with MQW (LED). Shown in FIG. 4 is the raw spectral data and a least square fit by a Gaussian function. It is apparent from FIG. 4 that the amplitude of the fringes in the raw spectral data may prevent accurate extraction of peak wavelength, FWHM, or peak intensity using such a Gaussian spectral luminescence profile as a fit. The case shown is for GaN-on-sapphire. It is to be noted that the modulation fringes observed on the measured luminescence spectrum would be much worse in the case of a Silicon substrate (GaN-on-Si LED technology), which is an important emerging material system for the LED industry that may help lowering the manufacturing costs which currently limit the wide adoption of high brightness LED for general lighting.

Figure 5:
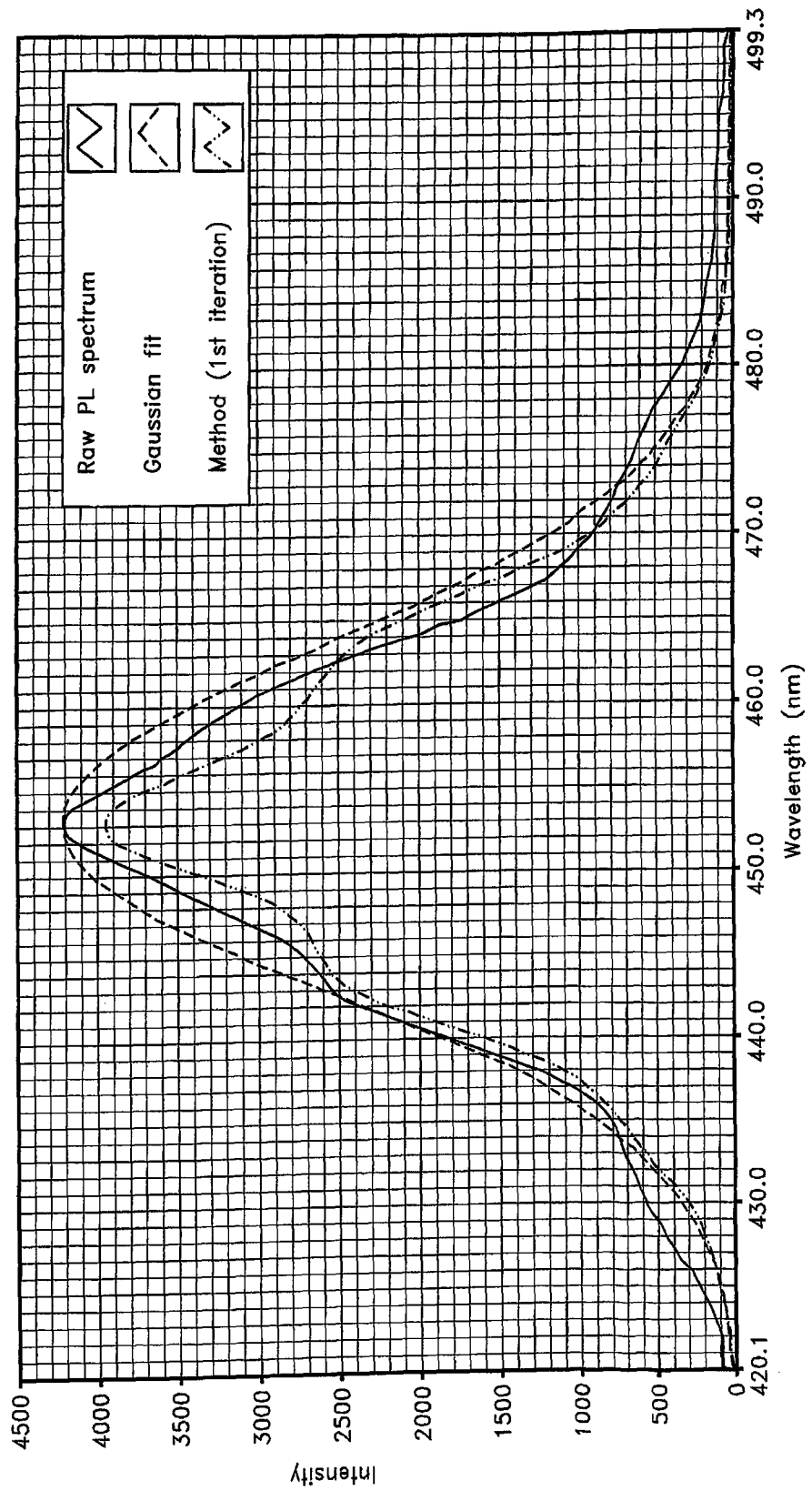
FIG. 5 shows an example of an improved fit to the measured photoluminescence spectrum using one of the methods disclosed herein.

FIG. 5 also shows an example of an improved fit to the measured photoluminescence spectrum using one of the methods disclosed herein. In particular, the method used was the method 100 described above in relation to FIG. 1. An ad hoc epi thickness (i.e. a rough estimate for the epi thickness) was used, and the Gaussian fit was used for the initial line shape and position. The output was modeled using the expression for $I_{total}(\lambda,t)$ in Appendix A. The improved match is shown as the curve labeled "Method ($1^{st}$ iteration)". The reasonable agreement in the spectral features seen after the first iteration provides support that the Fabry-Perot PL induced fringe modulation per FIG. 3 and Appendix A is indeed occurring and can be properly addressed by using the present method. It is to be noted that a much better convergence and agreement with the measured PL spectrum could be obtained by not using the constraint of a Gaussian emission line shape (the MQW emission line is generally not Gaussian). Also limiting in this example is the use of the simplest form of equations (as described in appendix A) that may also limit the quality of the convergence. A more complete implementation of the method may also account for a range of illumination ray angles and other details of the experimental setup (spectrometer calibration in intensity, not only wavelength) and sample (index as a function of wavelength "dispersion curve" used, as opposed to constant index as assumed here).

Figure 6:
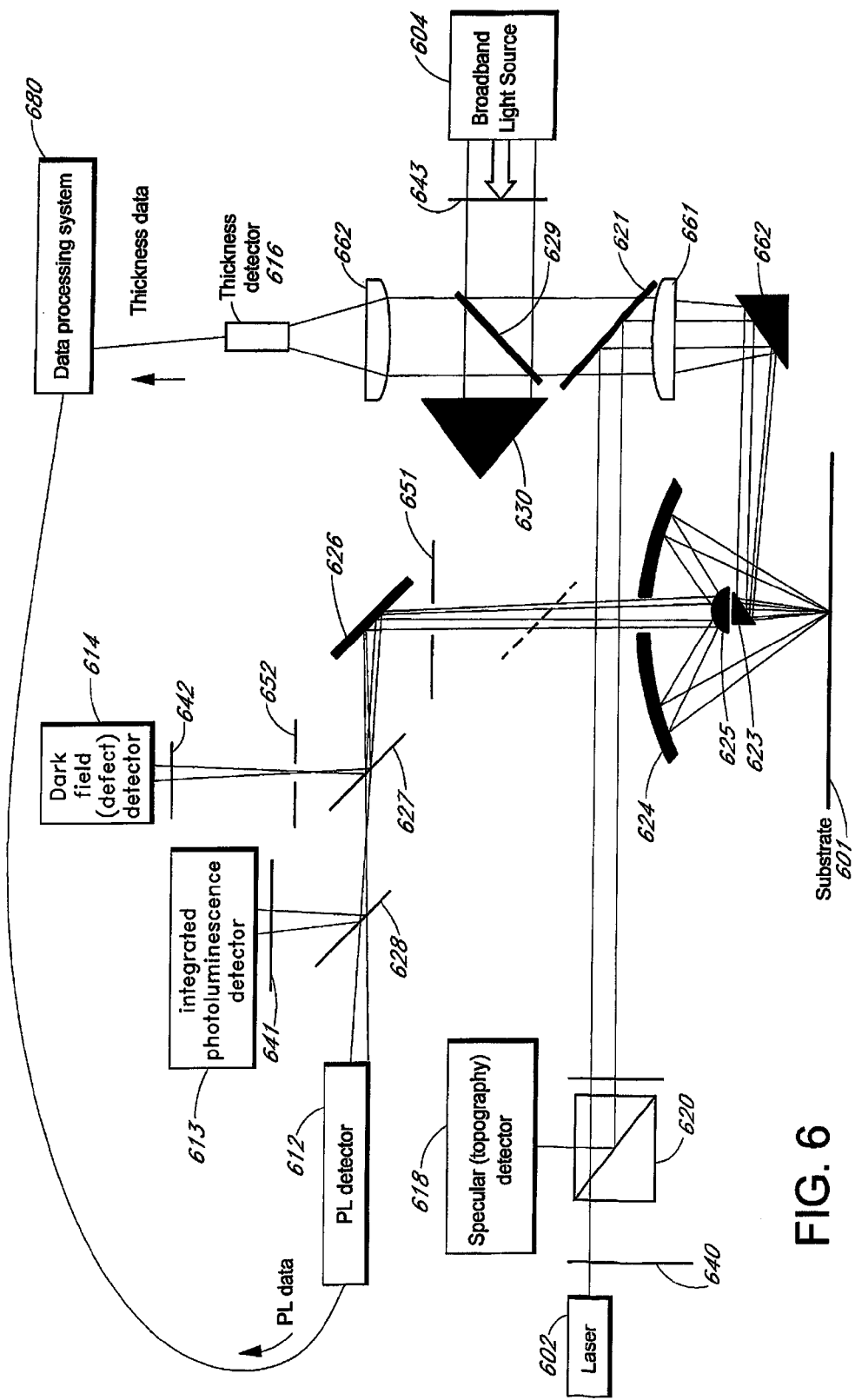
FIG. 6 shows a high-level diagram of an example apparatus for simultaneously measuring photoluminescence spectra, epitaxial layer thicknesses as well as the defectivity and topography of the epi layer in accordance with an embodiment of the invention.

FIG. 6 shows a high-level diagram of an example apparatus 600 for simultaneously measuring photoluminescence spectra and epitaxial layer thicknesses in accordance with an embodiment of the invention. The apparatus 600 measures the PL spectra and epi thicknesses from a target substrate 601 that is held by a stage, where the stage may be controllably moved for scanning purposes.

As depicted, the apparatus 600 may include a laser source 602 and a broadband light emitting diode (for example a white LED) or other broadband light source 604. The apparatus 600 may further include a spectral photoluminescence (PL) detector 612, an integrated photoluminescence detector 613 (that optically sums a portion of the luminescence a broad wavelength band, such as, for example, 420-500 nm, onto one detector, hereby mapping the overall brightness level of the PL), a dark field (defect) detector 614, an epitaxial thickness detector 616, and a specular (topography) detector 618. The laser source 602 may be the source for defect detection and photoluminescence measurements using the spectral PL detector 612, integrated PL detector 613, dark field detector 614 and the specular detector 618. The broadband source 604 may be the source for the epi thickness measurement using the epitaxial thickness detector 616.

The sources, target substrate, and detectors are optically interconnected using various optical elements. As shown in the example configuration depicted in FIG. 6, the various optical elements may include reflective mirrors (622, 623, 624, 625, and 626), partially reflective mirrors (621, 627, 628, and 629), optical filters 640, 641, 642, and 643), apertures (651 and 652), beam dump (630) and lenses (661 and 662).

While one optical configuration is shown in FIG. 6, other optical configurations may be used. In one alternate embodiment, the thickness detection method is broadband reflectometry in the red region of the spectrum while the spectra luminescence detection is in the blue region of the spectrum. This advantageously allows one to use a single spectrometer to measure both the thickness and the spectral luminescence, allowing reduction in apparatus cost and complexity. It also constitutes a notable improvement over current PL and Thickness mapping production metrology instruments that typically require two passes over the sample, as they measure PL and thickness data sequentially.

Figure 7:
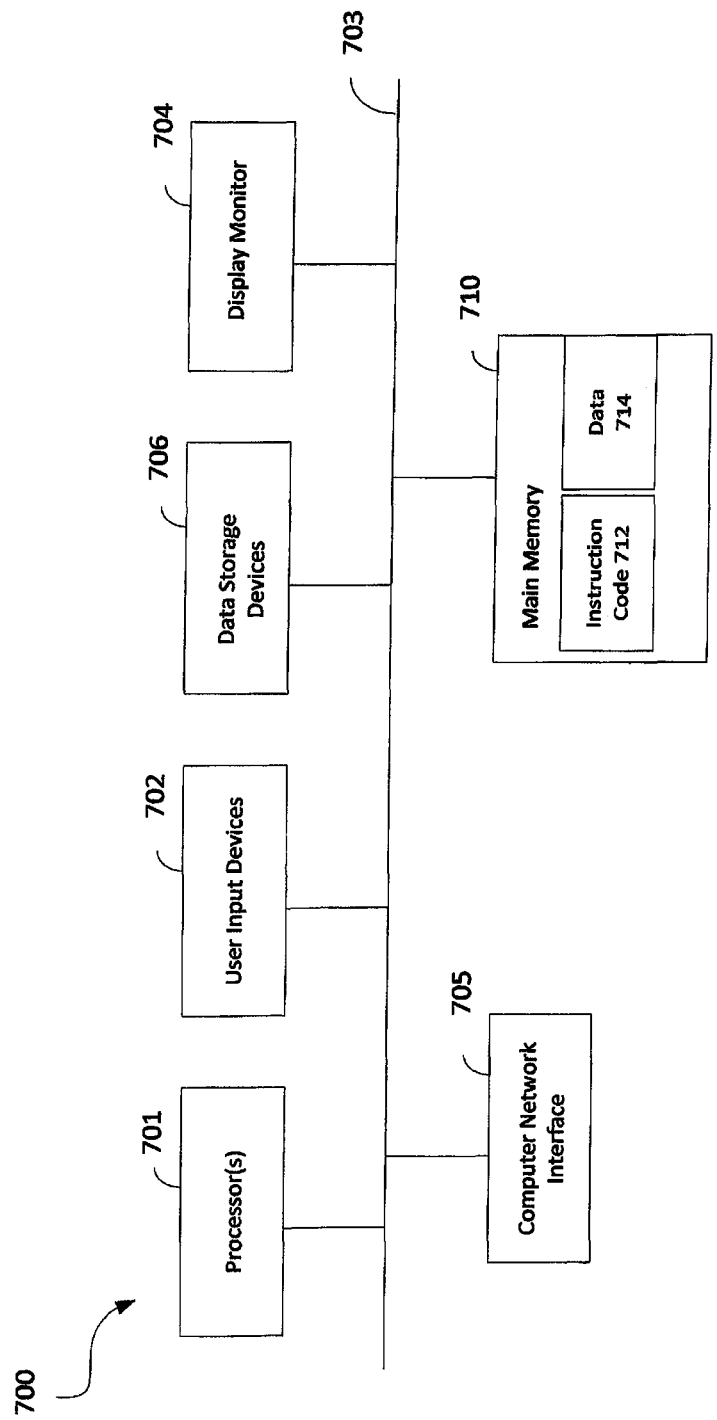
FIG. 7 depicts a simplified form of an example computer apparatus 700 in accordance with an embodiment of the invention.

FIG. 7 depicts a simplified form of an example computer apparatus 700 in accordance with an embodiment of the invention. Such a computer apparatus may be used, for example, to implement and perform any or all of the methods described above. This figure shows just one simplified example of such a computer apparatus.

As shown, the computer apparatus 700 may include one or more processors 701, such as those from the Intel Corporation of Santa Clara, Calif., for example. The computer apparatus 700 may have one or more buses 703 communicatively interconnecting its various components. The computer apparatus 700 may include one or more user input devices 702 (e.g., keyboard, mouse, etc.), a display monitor 704 (e.g., liquid crystal display, flat panel monitor, etc.), a computer network interface 705 (e.g., network adapter, modem), and a data storage system that may include one or more data storage devices 706 which may store data on a hard drive, semiconductor-based memory, optical disk, or other tangible non-transitory computer-readable storage media, and a main memory 710 which may be implemented using random access memory, for example.

In the example shown in this figure, the main memory 710 includes instruction code 712 and data 714. The instruction code 712 may comprise executable computer-readable program code (i.e., software) components which may be loaded from the tangible non-transitory computer-readable medium of the data storage device 706 to the main memory 710 for execution by the processor(s) 701. In particular, the instruction code 712 may be programmed to cause the computer apparatus 700 to perform the data processing steps in the methods described herein.

The above-described diagrams are not necessarily to scale and are intended be illustrative and not limiting to a particular implementation. In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

APPENDIX A

Let us consider here photoluminescence fringe/equations in the simplest parallel illumination case (Numerical aperture—or NA—equal to zero normal incidence (Angle of Incidence AOI—equal to zero), and single direction of emission of the PL light. This is a crude approximation as the MQW emits in all directions inside the epi layer, though the high index only allows a small portion of the light to escape around normal incidence (total internal reflection of rays above 20 degrees or so inside GaN). But the goal here is to illustrate the proposed method in its simplest implementation and we will thus proceed with calculating this case.

In our notation $$\varphi(\lambda, t) = 4\pi n_1(\lambda) \frac{t}{\lambda}$$

corresponds to the phase shift from the round-trip optical path of the electromagnetic wave (PL) through a thickness t of epi. Thus a phase of $\phi(\lambda,d/2)$ and $\phi(\lambda,t/2-d/2)$ for Up and Down PL respectively at the first interface they encounter (top and bottom of the epi, respectively). Up and Down refer to the upward and downward PL rays as shown schematically in FIG. 3.

To make the formula and calculations below more compact, we will simplify the reflectivity expression as follows:

$$r_1 \text{ as short for } r_1(\lambda, t) = \frac{n_1(\lambda, t) - 1}{n_1(\lambda, t) + 1}$$

and $$r_2 \text{ as short for } r_2(\lambda, t) = \frac{n_1(\lambda, t) - n_2(\lambda, t)}{n_2(\lambda, t) + n_1(\lambda, t)}$$

We then compute the amplitude of the light reflected from sample for Up ($E_1$) and Down ($E_2$) (we assume initial PL amplitude $E_{PL}$ from MQW as the same in both directions). We call its square $I_{PL}$ which corresponds to the PL intensity, function of the wavelength. $I_{PL}$ is directly proportional to the underlying luminescence spectrum that we refer to in the text. The total radiated MQW PL inside the epi (the "cavity") is 2. $I_{PL}$ in this convention, as the PL emitted in the down and up directions are assumed to be incoherent.

$$E_1(\lambda, t, d) = E_{PL}(\lambda) \cdot \sqrt{1 - r_1^2} \, e^{i\varphi(\lambda,d/2)} [1 + e^{i\varphi} r_1 r_2 + e^{i2\varphi}(r_1 r_2)^2 + \ldots] =$$

$$\frac{E_{PL}(\lambda) \cdot \sqrt{1 - r_1^2} \, e^{i\varphi(\lambda,d/2)}}{1 - r_1 r_2 e^{i\varphi(\lambda,t)}}$$

Hence: $I_1(\lambda, t) = |E_1(\lambda, t, d)|^2 = \frac{1 - r_1^2}{|1 - r_2 r_1 e^{i\varphi(\lambda,t)}|^2} I_{PL} =$ $$\frac{1 - r_1^2}{[1 - r_2 r_1 \cos[\varphi(\lambda, t)]]^2 + [r_2 r_1 \sin[\varphi(\lambda, t)]]^2} I_{PL} = \frac{1 - r_1^2}{1 - 2r_2 r_1 \cos[\varphi(\lambda, t)] + r_1^2 r_2^2} I_{PL}$$

$$E_2(\lambda, t, d) = E_{PL}(\lambda) \cdot \sqrt{1 - r_1^2} \, r_2 e^{i\varphi(\lambda,t/2-d/2)}$$

$$[1 + e^{i\varphi} r_1 r_2 + e^{i2\varphi}(r_1 r_2)^2 + \ldots] = \frac{E_{PL}(\lambda) \cdot \sqrt{1 - r_1^2} \cdot r_2 e^{i\varphi(\lambda,t/2-d/2)}}{1 - r_1 r_2 e^{i\varphi(\lambda,t)}}$$

Hence: $I_2(\lambda, t) = |E_2(\lambda, t, d)|^2 = \frac{(1 - r_1^2) r_2^2}{|1 - r_2 r_1 e^{i\varphi(\lambda,t)}|^2} I_{PL} = r_2^2 I_1(\lambda, t)$ The total intensity measured above the epi for incoherent PL events is obtained:

$$I_{total}(\lambda, t) =$$

$$I_1(\lambda, t) + I_2(\lambda, t) = (1 + r_2^2) I_1(\lambda, t) = \frac{(1 - r_1^2)(1 + r_2^2)}{1 - 2r_2 r_1 \cos[\varphi(\lambda, t)] + r_1^2 r_2^2} I_{PL}$$

$$I_{total}(\lambda, t) = \frac{1 - r_1^2 + r_2^2 - r_1^2 r_2^2}{1 - 2r_2 r_1 \cos[\varphi(\lambda, t)] + r_1^2 r_2^2} I_{PL}(\lambda)$$

which is the formula we used to generate the first iteration shown in FIG. 5, as a simple Gaussian spectral shape was transformed by applying the spectral modulation calculated above. The thickness was chosen to best match the spectral features observed, in the spirit of the minimization shown in block 208 of FIG. 2. The goal here is to illustrate how the Fabry-Perot and physical thickness-based computation constitutes a physically legitimate approach to removing the spurious fringes from the measured PL spectrum. A more complete implementation of the proposed method would include a more realistic line shape than Gaussian, a more complete computational form of the equations above (e.g. integrating of range of angles for incident illumination and radiated MQW light), possible re-absorption effects in the MQW, etc.

What is claimed is:

1. A computer-implemented method of processing a spectral luminescence map for a target substrate which has an epitaxial layer stack that includes a multiple quantum well, the method comprising:
   performing a measurement to obtain a measured spectral luminescence for a location on the target substrate;
   constraining a line shape for an underlying local luminescence spectrum;
   generating a computed spectral luminescence for the location using a seed epi layer thickness value; and
   determining a local thickness parameter and parameters of the underlying local luminescence spectrum so as to minimize a difference between the computed spectral luminescence and the measured spectral luminescence for the location.

2. The method of claim 1, wherein the computed spectral luminescence is a multiplication of the underlying local luminescence spectrum and a local spectral modulation, further wherein the local spectral modulation is generated by a Fabry-Perot cavity type computation based on the local thickness parameter.

3. The method of claim 2, wherein the parameters of the underlying local luminescence spectrum include a peak wavelength for the location.

4. The method of claim 3 wherein the parameters of the underlying local luminescence spectrum further include a peak intensity and a full-width at half-maximum (FWHM) for the location.

5. The method of claim 1, wherein the luminescence mapping data comprises photoluminescence mapping data.

6. The method of claim 1, wherein the luminescence mapping data comprises electroluminescence mapping data.

7. The method of claim 1, wherein the seed epi layer thickness value comes from prior knowledge or a prior measurement.

8. An apparatus for performing spectral luminescence measurements on a target substrate and processing spectral luminescence mapping data obtained from the target substrate, the target substrate having an epitaxial layer stack that includes a multiple quantum well, the apparatus comprising:
   a processor for executing computer-readable instruction code so as to process data;
   data storage for storing non-transitory computer-readable instruction code and the data; and
   non-transitory computer-readable instruction code stored in the data storage for
      performing a measurement to obtain a measured spectral luminescence for a location on the target substrate,
      constraining a line shape for an underlying local luminescence spectrum,
      generating a computed spectral luminescence for the location using a seed epi layer thickness value, and
      determining a local thickness parameter and parameters of the underlying local luminescence spectrum so as to minimize a difference between the computed spectral luminescence and the measured spectral luminescence for the location.

9. The apparatus of claim 8, wherein the computed spectral luminescence is a multiplication of the underlying local luminescence spectrum and a local spectral modulation, further wherein the local spectral modulation is generated by a Fabry-Perot cavity type computation based on the local thickness parameter.

10. The apparatus of claim 9, wherein the parameters of the underlying local luminescence spectrum include a peak wavelength for the location.

11. The apparatus of claim 10, wherein the parameters of the underlying local luminescence spectrum further include a peak intensity and a full-width at half-maximum (FWHM) for the location.

12. The apparatus of claim 8, wherein the luminescence mapping data comprises photoluminescence mapping data.

13. The apparatus of claim 8, wherein the luminescence mapping data comprises electroluminescence mapping data.

14. The apparatus of claim 8, wherein the seed epi layer thickness value comes from prior knowledge or a prior measurement.

* * * * *